United States Patent [19]
Korn et al.

[11] Patent Number: 5,792,887
[45] Date of Patent: Aug. 11, 1998

[54] DECARBOXYLATION PROCESS

[75] Inventors: Stewart Reid Korn, Rochdale; Michael Scott Howarth, Littleborough; Gordon Jamieson, East Lothian, all of United Kingdom

[73] Assignee: Zeneca Limited, London, Great Britain

[21] Appl. No.: 702,482

[22] PCT Filed: Feb. 17, 1995

[86] PCT No.: PCT/GB95/00335

§ 371 Date: Nov. 4, 1997

§ 102(e) Date: Nov. 4, 1997

[87] PCT Pub. No.: WO95/24373

PCT Pub. Date: Sep. 14, 1995

[30] Foreign Application Priority Data

Mar. 8, 1994 [GB] United Kingdom ............... 9404574

[51] Int. Cl.⁶ ........................................... C07C 51/38
[52] U.S. Cl. ........................................... 562/479
[58] Field of Search ............................... 562/479

[56] References Cited

U.S. PATENT DOCUMENTS 4,782,180  11/1988  Wemple et al. ............... 562/479
5,233,085  8/1993  O'Reilly et al.

FOREIGN PATENT DOCUMENTS

| 0 415 585 A1 | 3/1991 | European Pat. Off. ...... C07C 229/58 |
| 429 848 | 6/1991 | European Pat. Off. |
| 431 294 | 6/1991 | European Pat. Off. |
| 3621 707 A1 | 1/1988 | Germany ...................... C07C 63/70 |
| 125 737 | 1/1989 | Japan .......................... C07B 37/06 |
| 2 122 190 | 1/1984 | United Kingdom. |

OTHER PUBLICATIONS

Wang et al, Chemical Abstracts, vol. 79, No. 15, 91729 (1973).

Shusuke et al, Chemical Abstracts, vol. 111, 96836 (1989).

*Primary Examiner*—Paul J. Killos
*Attorney, Agent, or Firm*—Pillsbury Madison & Sutro LLP

[57] ABSTRACT

A process for the monodecarboxylation of a halogenated aromatic dicarboxylic acid or derivative thereof in which the halogenated aromatic dicarboxylic acid or derivative thereof in a liquid medium is heated characterized in that the liquid medium is a polar aprotic liquid medium.

14 Claims, No Drawings

DECARBOXYLATION PROCESS

This application claims benefit of international application PCT/GB95 /00335, filed Feb. 17, 1995.

This invention relates to a process for decarboxylation particularly for the monodecarboxylation of halogenated aromatic dicarboxylic acids and derivatives thereof.

JP 01 25,737 discloses a process for monodecarboxylating 3,4,5,6-tetrafluorophthalic acid in a tertiary amine at temperatures at 130° C.

A decarboxylation process is disclosed in GE 2122190 in which both carboxylic acid groups in 2,3,5,6-tetrafluoroterephthalic acid or both ester groups in 2,3,5,6-tetrachloroterephthalic acid dimethyl ester are removed to form 1,2,4,5-tetrafluoro- or 1,2,4,5-tetrachlorobenzene respectively.

The present invention seeks to provide a process for monodecarboxylation of certain halogenated aromatic dicarboxylic acids and derivatives thereof under mild process conditions and in high yields.

According to the present invention there is provided a process for the monodecarboxylation of a halogenated aromatic dicarboxylic acid or derivative thereof in which the halogenated aromatic dicarboxylic acid or derivative thereof in a liquid medium is heated characterised in that the liquid medium is a polar aprotic liquid medium.

This process has the advantage that it may be readily controlled such that little or no doubly decarboxylated product is formed and gives high yields of monodecarboxylated product. The process has the further advantage that no catalysts such as metal or metal salts are required to effect decarboxylation.

The halogenated aromatic dicarboxylic acid is preferably a halogenated benzene dicarboxylic acid of the Formula 1:

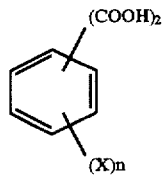

Formula 1 in which
each X independently is halogen; and
n is an integer from 1 to 4.
Where X is halogen it is preferably -F or -Cl.
n is preferably 4.

Preferred halogenated benzene dicarboxylic acids of Formula 1 are preferably those in which the -COOH groups are in the 1- and 3-, or the 1- and 4- positions more preferably in the 1- and 4- positions.

Preferred 1,4- (COOH)$_2$ compounds of Formula 1 are those in which X is -F or -Cl and n=4, especially those in which X is -F and n =4.

An especially preferred compound of Formula 1 is 2,3,5,6-tetrafluoroterephthalic acid.

The polar aprotic medium may be selected from amides such as dimethylformamide or dimethylacetamide; N-heterocyclics such as N-methylpyrollidinone; S-heterocyclics such as sulpholane; and ethers such as dimethoxyethane. Preferred polar aprotic media are amides, particularly dimethylformamide and dimethylacetamide. The process may be performed at a temperature from 40° C. to 80° C., preferably at a temperature from 50° C. to 75° C. and especially at 55° C. to 75° C.

The product may be isolated from the reaction mixture by conventional techniques such as cooling the reaction mixture, adding water and collecting precipitated product by filtration.

The halogenated aromatic dicarboxylic acids may be conveniently prepared by the acid hydrolysis of the corresponding halogenated aromatic dinitriles for example 2,3,5,6-tetrafluoroterephthalic acid may be prepared by hydrolysis of 2,3,5,6-tetrafluoro-terophthalodinitrile in a mixture of sulphuric and glacial acetic acids at 175° C.

The invention is illustrated by the following example:

EXAMPLE 1

Preparation of 2,3,5,6-tetrafluorobenzoic Acid

N,N-Dimethylacetamide (14.0 parts) and 2,3,5,6-tetrafluoroterephthalic acid (2.91 parts) was heated at 70° C. for 4 hours before cooling to 20° C. adding water (7 parts) and cooling to 5° C. The precipitated solid was collected by filtration and washed with cold water and dried, the aqueous filtrates were evaporated under vacuum and the resultant solids combined to give 2,3,5,6-tetrafluorobenzoic acid (98%). 1,2,4,5-tetrafluorobenzene (2%) was also formed.

We claim:

1. A process for the monodecarboxylation of a halogenated dicarboxylic acid of Formula (1) or derivative thereof:

Formula (1)

in which
each X independently is halogen; and
n is an integer of from 1 to 4
which comprises heating the halogenated dicarboxylic acid or derivative thereof in a polar aprotic liquid medium at a temperature of from 40° C. to 80° C. whereby the acid is monodecarboxylated.

2. A process according to claim 1, wherein X is Cl or F.

3. A process according to claim 1 wherein n is 4.

4. A process according to claim 1 wherein the polar aprotic medium is selected from the group consisting of amides and N-heterocyclics.

5. A process according to claim 4, wherein the polar aprotic medium is selected from the group consisting of dimethylformamide and dimethylacetamide.

6. A process according to claim 1 in which the compound of Formula (1) is 2,3,5,6-tetrafluoroterephthalic acid.

7. A process according to claim 1 wherein X is F, n is 4 and the polar aprotic medium is selected from the group consisting of dimethylformamide and dimethylacetamide.

8. A process according to any one of claims 1 to 7, wherein the process is performed at a temperature of from 55°–75° C.

9. A process for the preparation of a halogenated benzoic acid of formula:

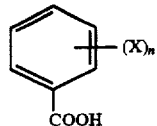

or a derivative thereof:
wherein:
each X independently is halogen; and
n is an integer of from 1 to 4, said process comprising acid hydrolysis of a compound of formula:

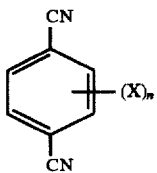

to produce a compound of Formula (1):

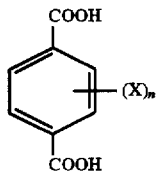   Formula (1)

or a derivative thereof, and subsequently monodecarboxylating the compound of Formula (1), or a derivative thereof by heating the compound of Formula (1) at a temperature of from 40° C. to 80° C. in a polar aprotic liquid medium.

10. A process according to claim 9, wherein X is Cl or F.

11. A process according to claim 9, wherein n is 4.

12. A process according to claim 9, wherein the polar aprotic medium is selected from the group consisting of amides and N-heterocyclics.

13. A process according to claim 12, wherein the polar aprotic medium is selected from the group consisting of dimethylformamide and dimethylacetamide.

14. A process for the preparation of 2,3,5,6-tetrafluorobenzoic acid wherein 2,3,5,6-tetrafluoroterephthalic acid is prepared by acid hydrolysis of 2,3,5,6-tetrafluorophthalodinitrile, and the 2,3,5,6-tetrafluoroterephthalic acid so prepared is monodecarboxylated by heating at a temperature of from 40° to 80° C. in a polar aprotic medium selected from the group consisting of dimethylformamide and dimethylacetamide.

* * * * *